(12) United States Patent
Mao

(10) Patent No.: US 7,709,442 B2
(45) Date of Patent: May 4, 2010

(54) IN VIVO SYNTHESIS OF CONNECTIVE TISSUES

(75) Inventor: Jeremy Jian Mao, Closter, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 12/119,631

(22) Filed: May 13, 2008

(65) Prior Publication Data

US 2008/0288085 A1 Nov. 20, 2008

Related U.S. Application Data

(62) Division of application No. 10/940,080, filed on Sep. 14, 2004, now Pat. No. 7,375,077.

(60) Provisional application No. 60/504,234, filed on Sep. 19, 2003.

(51) Int. Cl.
*A61K 45/00* (2006.01)
*A61K 38/18* (2006.01)
*A61K 38/19* (2006.01)
*A61K 47/36* (2006.01)
*A61F 2/02* (2006.01)
*A61F 2/08* (2006.01)

(52) U.S. Cl. .................... 514/2; 424/423; 424/426; 424/491; 424/492; 424/93.7

(58) Field of Classification Search .................. None
See application file for complete search history.

(56) References Cited

U.S. PATENT DOCUMENTS

| 4,841,962 | A | 6/1989 | Berg et al. |
| 5,282,859 | A | 2/1994 | Eisenberg |
| 5,284,655 | A | 2/1994 | Bogdansky et al. |
| 5,700,289 | A | 12/1997 | Breitbart et al. |
| 5,939,323 | A | * 8/1999 | Valentini et al. ............ 435/395 |
| 6,090,117 | A | 7/2000 | Shimizu |
| 6,350,867 | B1 | 2/2002 | Hart et al. |

(Continued)

FOREIGN PATENT DOCUMENTS

EP 0702081 3/1996

(Continued)

OTHER PUBLICATIONS

Alhadlaq et al, Adult stem cell driven genesis of human-shaped articular condyle, Annals of Biomedical Engineering, vol. 32, p. 911-23 (2004).

(Continued)

*Primary Examiner*—Cherie M Woodward
(74) *Attorney, Agent, or Firm*—Sonnenschein Nath & Rosenthal LLP

(57) ABSTRACT

The in vivo synthesis of connective tissue by fibroblast or fibroblast precursor cells ensconced within a biocompatible scaffold is disclosed. The cells are preferably present in a biocompatible scaffold such as gelatin and placed between two other biocompatible scaffolds such as collagen sponges soaked with a collagenic amount of a member of the TGF-β family of proteins. This composition is then implanted in a host to produce cranial sutures, periodontal ligament or other fibrous tissue structures in vivo.

19 Claims, 4 Drawing Sheets

U.S. PATENT DOCUMENTS

| | | | |
|---|---|---|---|
| 2001/0038848 A1 | 11/2001 | Donda et al. | |
| 2002/0022883 A1 | 2/2002 | Burg | |
| 2002/0127265 A1* | 9/2002 | Bowman et al. | 424/426 |
| 2002/0192263 A1 | 12/2002 | Merboth et al. | |
| 2003/0180344 A1 | 9/2003 | Wise et al. | |
| 2003/0185752 A1 | 10/2003 | Nathan et al. | |
| 2003/0185871 A1 | 10/2003 | Nathan et al. | |
| 2005/0042254 A1 | 2/2005 | Freyman et al. | |

FOREIGN PATENT DOCUMENTS

| | | |
|---|---|---|
| EP | 1022031 | 7/2000 |
| EP | 1022031 A1 * | 7/2000 |
| WO | 99/60951 | 12/1999 |
| WO | 01/25402 | 4/2001 |

OTHER PUBLICATIONS

Einhorn, The cell and molecular biology of fracture healing, Clinical Orthopaedics and Related Research, vol. 355S, p. S7-S21 (1998).

Enlow, Normal craniofacial growth, in: Craniosynostosis: Diagnosis, Evaluation and Management, Cohen MM, Oxford University Press, New York, NY, vol. 6, p. 132-56 (1986).

Gazit et al, Engineered pluripotent mesenchymal cells integrate and differentiate in regenerating bone: a novel cell-mediated gene therapy, Journal of Gene Medicine, vol. 1, p. 121-133 (1999).

Goldberg and Caplan, Biological resurfacing: an alternative to total joint arthroplasty, Orthopedics, vol. 17, p. 819-21 (1994).

Hunziker, Articular cartilage repair: basic science and clinical progress. A review of the current status and prospects, Osteoarthritis and Cartilage, vol. 10, p. 432-63 (2002).

Hong et al, Tissue-engineered rabbit cranial suture from autologous fibroblasts and BMP2, J Dental Res, vol. 83(10), p. 751-756 (2004).

Kimura et al, Adipose tissue engineering based on human preadipocytes combined with gelatin microspheres containing basic fibroblast growth factor, Biomaterials, vol. 24(14), p. 2513-2521 (2003).

Kokich, The biology of sutures, in: Craniosynostosis: Diagnosis, Evaluation and Management, Cohen MM, Oxford University Press, New York, NY, vol. 4, p. 81-103 (1986).

Mao, Mechanobiology of craniofacial sutures, J Dent Res, vol. 81, p. 810-6 (2002).

Mardas et al, Bone and suture regeneration in calvarial defect by e-PTFE-membranes and demineralized bone matrix and the impact of calvarial growth: an experimental study in the rat, Journal of Craniofacial Surgery, vol. 13, p. 453-64 (2002).

Marsh, Surgical research on craniosynostosis, In: Craniosynostosis: Diagnosis, Evaluation and Management, 2nd Edition, Cohen MM, Oxford University Press, New York, NY, vol. 21, p. 292-308 (2000).

Mooney et al, Correction of coronal suture synostosis using suture and dura mater allografts in rabbits with familial craniosynostosis, Cleft Palate-Craniofacial Journal, vol. 38, p. 206-25 (2001).

Moss, Growth of the calvaria in the rat, Am J Anat, vol. 94, p. 333-361 (1954).

Mow et al, Structure and function of articular cartilage and meniscus, Basic Orthopaedic Biomechanics, Raven Press, New York, NY, vol. 4, p. 143-9 (1991).

Nakahara et al, Novel approach to regeneration of periodontal tissues based on in situ tissue engineering: effects of a controlled release of basic fibroblast growth factor from a sandwich membrane, Tissue Engineering, vol. 9(1), p. 153-162 (2003).

Opperman, Cranial structures as intramembranous bone growth sites, Developmental Dynamics, vol. 219, p. 472-485 (2002).

Opperman et al, Transforming growth factor-beta 3 (TGF-beta3) in a collagen gel delays fusion of the rat posterior interfrontal suture in vivo, Anatomical Record, vol. 267(2), p. 120-130 (2002).

Posnick, Craniosynostosis and the craniofacial dysostosis syndromes: current surgical management, In: Craniosynostosis: Diagnosis, Evaluation and Management, 2nd Edition, Cohen MM, Oxford University Press, New York, NY, vol. 2, p. 269-291 (2000).

Pritchard et al, The structure and development of cranial and facial sutures, J Anat, vol. 90, p. 73-86 (1956).

Steadman's Medical Dictionary, 27th Ed, Lippincott Williams and Wilkins (2000).

Tessier, Craniofacial surgery in syndromic craniosynostosis, In: Craniosynostosis: Diagnosis, Evaluation and Management, 2nd Edition, Cohen MM, Oxford University Press, New York, NY, p. 228-268 (2000).

Volk et al, Regulating the regulators of chrondrocyte hypertrophy, Journal of Bone and Mineral Research, vol. 14, p. 483-486 (1999).

International Search Report issued on Mar. 27, 2006, in related application PCT/US04/30091.

European Search Report issued on Sep. 23, 2008, in related application EP 04788757.

Office Action issued on Jan. 14, 2010 by the EPO in the related application EP 04 788 757.5.

* cited by examiner

IN VIVO SYNTHESIS OF CONNECTIVE TISSUES

CROSS-REFERENCE TO RELATED APPLICATION

This application is a divisional application of U.S. application Ser. No. 10/940,080 filed on Sep. 14, 2004, now U.S. Pat. No. 7,375,077, which claims the benefit of U.S. Provisional Application Ser. No. 60/504,234 filed on Sep. 19, 2003, each of which are incorporated herein by reference in their entirety.

GOVERNMENTAL SUPPORT

The present invention was made with governmental support pursuant to USPHS grants DE13964 and DE15391 from the National Institute of Dental and Craniofacial Research of the National Institutes of Health. The government has certain rights in the invention.

TECHNICAL FIELD

This invention relates to the formation of fibrous soft connective tissue in vivo. More particularly, this invention relates to the synthesis of cranial sutures by growth factors, fibroblast-like cells and stem cells encased within a biocompatible scaffold.

BACKGROUND OF THE INVENTION

Fibrous tissue consists of fibroblastic cells embedded in a hydrated extracellular matrix [Mow et al., *Basic Orthopaedic Biomechanics*, New York, Raven Press, 143-199 (1991)]. Fibroblasts are crucial to fibrous tissue histogenesis and maintenance [Hunziker (2000) *Osteoarth. Cartil.*, 10:432-463]. Mature fibrous tissue only has a limited number of resident fibroblasts [Volk et al., (1999) *Bone Miner. Res.*, 14:483-486].

There is overwhelming evidence that adult bone marrow contains mesenchymal stem cells (MSCs) that can differentiate into virtually all lineages of connective tissue cells such as osteogenic cells, chondrogenic cells, tenocytes, adipogenic cells, odontoblastic cells, etc. [Goldberg et al. (1994) *Orthopedics*, 17:819-821]. The MSCs' role in wound healing involves multiple phenotypic switches between fibrous, hyaline cartilage, fibro-cartilage, and bone [Einhorn (1998) *Clin. Orthop.*, 355 Suppl., S7-S21]. The techniques of harvesting and culturing MSCs from bone marrow as well as inducing MSCs to differentiate into chondrogenic and osteogenic cell lineages in vitro and in vivo have been successful. [Alhadlaq et al. (2003) *Ann. Biomed. Eng.* 32(7): 911-923].

Cranial sutures are the soft connective tissues located between mineralized calvarial bones in the skull. These structures share the common feature of interosteal linkage; i.e., these fibrous tissues link bone to bone.

Cranial sutures permit the expansive growth of the brain and calvarial bones of the skull during childhood and adolescence [Enlow, (1999) In: Cohen M M Jr., MacLean R E (Eds.) *Craniosynostosis: Diagnosis Evaluation and Management*, New York: Raven Press. 131-156; and Mao (2002) *J. Dent. Res.*, 81:810-816]. Cranial sutures are comprised of fibroblast-like cells derived from the neural crest [Pritchard et al (1956) *J Anat* 90:73-86]. Theses cells lie within a vascularization-rich matrix that is sandwiched between osteoblast-lined bone formation fronts [Opperman, (2000) Dev. Dyn., 219:472-485].

Craniosynostosis is the premature ossification and mineralization of sutures before cranial, facial, and brain growth is completed [Cohen (2000) In: Cohen M M Jr. (Ed.) *Craniosynostosis: Diagnosis Evaluation and Management* New York, Raven Press 81-103]. This congenital disorder arises in approximately one of every 2,500 live human births (Cohen, Ibid.). Craniosynostosis can manifest as visible craniofacial disfigurations and grossly elevated intracranial pressure leading to severe neurological disorders such as mental retardation, blindness, and seizures (Cohen, Ibid.).

At the present time, craniofacial surgery is the only alternative for correcting visible craniofacial disfigurations and relieving abnormally high intracranial pressure [Marsh (2000) In: Cohen and MacLean (Eds), *Craniosynostosis: Diagnosis Evaluation and Management*, Oxford University Press, New York, 292-308; Posnick, (2000) In: Cohen and MacLean (Eds), *Craniosynostosis: Diagnosis Evaluation and Management*, Oxford University Press, New York 269-291; and Tessier (2000) In: Cohen and MacLean (Eds *Craniosynostosis: Diagnosis Evaluation and Management*. Oxford University Press, New York, 228-268]. Surgeons typically perform craniotomy surgery in early childhood by physically dissecting the fused sutures in the skull and creating gaps of empirical sizes between involved calvarial bones with the hope that the surgically created gaps may accommodate all remaining brain growth and calvarial bone growth in the child (Marsh, 2000, Ibid.; and Tessier, 2000, Ibid.).

Due to the unpredictability of craniofacial growth from the time of the first surgical correction during infancy until growth completion during adolescence, surgically created gaps often re-synostose. Therefore, multiple additional surgeries may be needed to correct the re-synostosis. This problem occurs because the synostosed suture with missing fibrous interface was replaced by a surgically created gap still lacking sustainable fibrous component (Marsh, 2000, Ibid.; and Tessier, 2000, Ibid.).

Previous attempts at cranial suture transplantation have not been successful. For example, although surgical replacement of synostosed rabbit suture with an allogeneic suture graft including dura mater from the wild type rabbit permits postoperative sutural growth [Mooney et al. (2001) *Cleft Palate Craniofac. J.*, 38:206-225]. However, this allogeneic suture transplantation approach necessitates creation of secondary bony defects, questionable donor availability and potential immune rejection when human applications are considered. Another effort to heal a surgically created defect involving the rat sagittal suture and adjacent bone by e-PEFE membrane with ruminants of suture-like structures [Marda et al. (2002) *J. Craniofac. Surg.*, 13:453-462] suffered because it is believed that the observed suture-like structure in the defect originated from the remaining portion of the host sagittal suture. Lastly, although mechanical and chemical disturbances of surgically created calvarial defects involving at least one cranial suture lead to incomplete healing [Moss (1954) *Am. J. Anat.*, 94:333-361] it does not appear to be a clinically applicable model because the surgically created bony gap in craniosynostosis patients should ideally be healed by the completion of craniofacial growth. As discussed hereinafter, the present invention can overcome many of these problems and can improve upon previous efforts of suture transplantation and delaying the rate of suture synostosis.

BRIEF SUMMARY OF THE INVENTION

The present invention provides engineered connective tissue generated in vivo by use of a composition comprising a biocompatible scaffold that contains dispersed collagenous precursor cells such as fibroblastic (collagenoblastic) cells or fibroblast precursor, stem cells such as embryonic stem cells or adult stem cells derived from bone marrow, adipose tissue, peripheral blood or other tissue that are preferably autologous along with an effective amount of growth factor(s). In a preferred embodiment, that biocompatible scaffold is comprised of gelatin that is sandwiched between two further biocompatible scaffolds comprised of microporous collagen sponges one or both of which can be loaded with an effective amount of a growth factor such as recombinant human bone morphogenic protein 2 (rhBMP-2) or stem cells such as embryonic stem cells or adult stem cells that are preferably adult mesenchymal stem cells (MSCs) so that a tri-layered biocompatible scaffold composition is formed. More preferably, the cells are autologous.

Thus, one aspect of the present invention contemplates a composition of precursor cells such as dermal or other fibroblastic cells or their precursor stem cells such as embryonic stem cells or adult stem cells that are preferably adult MSCs that are culture-expanded and seeded in (dispersed within) a biocompatible scaffold such as a gelatin scaffold that is sandwiched between two other biocompatible scaffolds such as microporous collagen sponges loaded with an effective amount of a growth factor such as recombinant human BMP-2 (rhBMP-2), another growth factor as discussed below, or stem cells that can provide the growth factor. The collagenous precursor cells such as fibroblastic cells are preferably autologous and can be isolated subcutaneously from, but not limited to, the anterior tibial region. The composition can be surgically implanted in the center of the host parietal bone to provide for the in vivo synthesis of a cranial suture-like structure having microscopic characteristics reminiscent of the adjacent (natural) cranial suture.

Another embodiment of the present invention is a composition comprising a biocompatible polymer loaded with collagenous precursor cells such as fibroblastic cells. Still another embodiment is a method of producing connective tissue by in vivo implantation of a composition comprising a biocompatible scaffold and fibroblastic cells.

BRIEF DESCRIPTION OF THE DRAWINGS

In the drawings forming a part of this invention.

Figure 1:
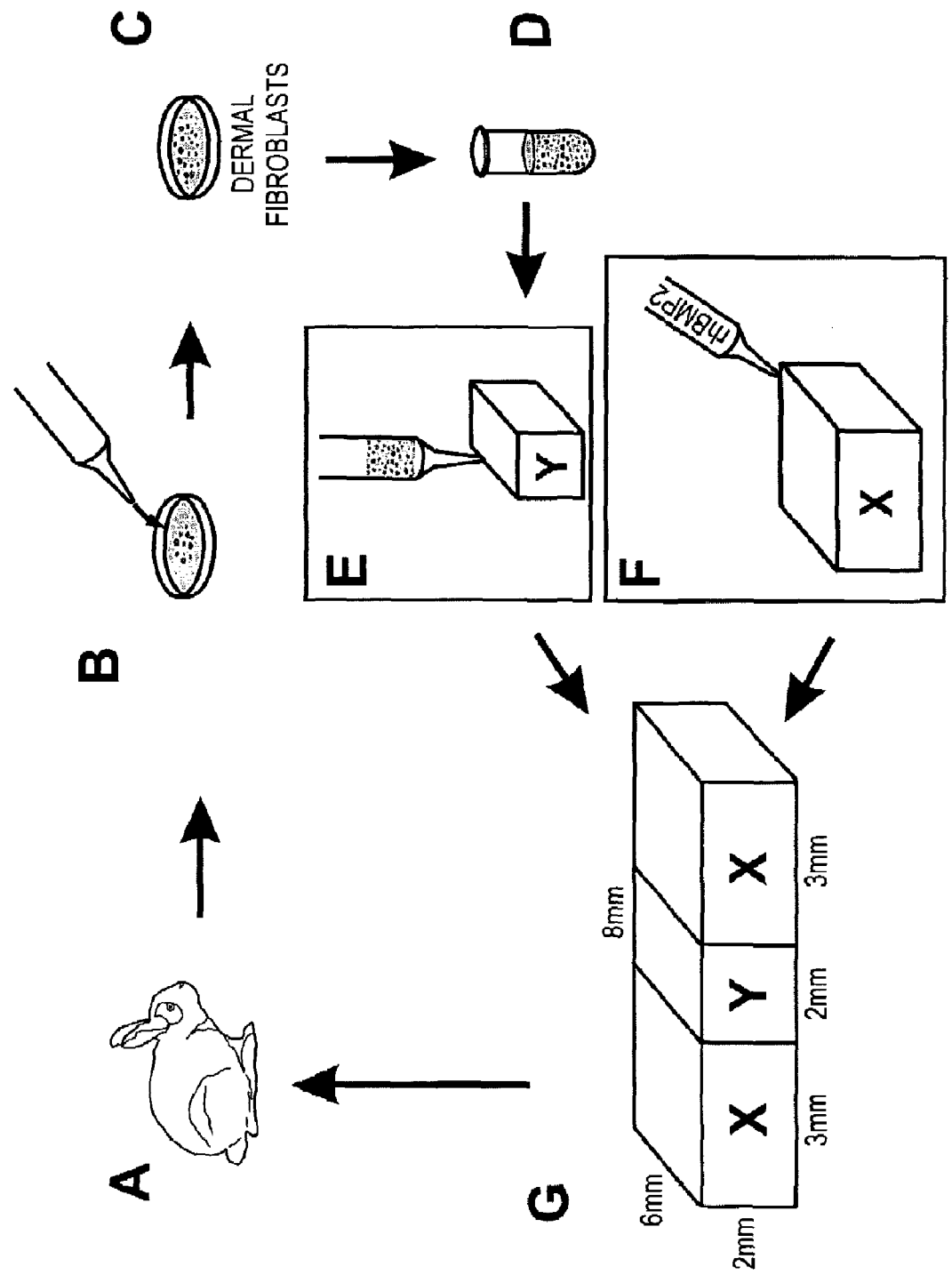
FIG. 1, in parts 1A-AF, is a diagram of the protocol followed in the isolation of dermal fibroblasts and fabrication of fibroblastic composition. 1A: A 5-mm incision was made in the anterior tibia and a small piece of subcutaneous fibrous tissue (approx. 3×3 mm$^2$) was removed. 1B: The fibrous tissue was enzyme digested, neutralized and filtered through a cell restrainer with 100 μm pore size. 1C: After centrifugation, the isolated dermal fibroblasts were plate-cultured and expanded in DMEM with 10% FBS and 1% antibiotic-antimycotic. 1D: Upon 90% confluency, the dermal fibroblasts were trypsinized, and loaded in cell suspension. 1E: An absorbable gelatin scaffold was trimmed into 2×2×6 mm$^3$ and immersed in the suspension of culture-expanded dermal fibroblasts at a density of 10$^7$ cells/ml in DMEM supplemented with 10% FBS, creating the Y component of the eventual composite tissue construct. 1F: Absorbable collagen hemostatic sponges were each trimmed into 3×2×6 mm$^3$ size. Recombinant human bone morphogenetic protein-2 (rhBMP-2) was prepared by dissolving 2.5 μg rhBMP-2 in 15 μl PBS at 4° C. overnight (about 18 hours), forming two X components of the eventual composite tissue construct. 1G: Dermal fibroblast-seeded gelatin scaffold (Y component) is sandwiched between two microporous collagen sponges soaked in rhBMP-2 (X components). Following creation of surgical calvarial defects in the corresponding rabbits that had donated dermal fibroblasts, composite tissue grafts were implanted into the center of the parietal bone devoid of natural cranial sutures (N=4). In a control group, tissue grafts consisting of rhBMP-2 soaked collagen sponges without dermal fibroblasts were implanted in age- and sex-matched rabbits (N=4).

The present invention has several benefits and advantages. One benefit is that the connective tissue generated in vivo can overcome deficiencies associated with current craniofacial surgery and associated re-mineralizations. An advantage of the invention is that use of its method and composition can provide a suture-like, fibrous tissue, interface between two adjacent bone surfaces. Still further benefits and advantages of the invention will be apparent to those skilled in this art from the detailed description that follows.

DETAILED DESCRIPTION OF THE INVENTION

The present invention relates to a composition comprising collagenous precursor cells such as fibroblastic cells or stem cells that can be embryonic or adult cells such as adult MSCs or a mixture of those cells dispersed in a biocompatible scaffold; i.e., a scaffold that is not rejected by the body of the host animal into which it is implanted, useful for in vivo synthesis of collagenous connective tissue. Such scaffold materials are well known to skilled workers and many are available commercially as is seen hereinafter.

Preferably, the connective tissue is synthesized by autologous fibroblastic cells, and those cells are utilized illustratively herein. Also preferred are fibroblastic cells derived from the dermis of a mammal, but can be obtained from any mammalian tissue in which such cells are present. More preferably, the connective tissue is synthesized from the fibroblastic cells that are contained within a biocompatible scaffold.

Stem cell precursors to fibroblasts can also be utilized such as embryonic or adult stem cells that are well known and need not be discussed herein. These cells can be obtained from bone marrow, adipose tissue and peripheral blood, as well as from other sources, as is also well known. Adult mesenchymal stem cells are preferred with the understanding that fetal stem cells or other adult stem cells can be used. The adult mesenchymal cells are derived from bone marrow cells that can differentiate into chondrocytes.

Stem cells are typically utilized along with a chondrogenic amount of a chondrogenic agent. A preferred chondrogenic agent is a TGFβ1, a member of the transforming growth factor-beta superfamily such as TGF-β1, or a vitamin A analog such as ascorbic acid.

Both soft and hard scaffolds have been used for bone engineering. Biocompatible hard scaffold materials, such as hydroxyapatite, can provide stiff mechanical support, whereas soft polymers, such as hydrogels, permit more homogenous cell seeding and room for the formation of bone matrix in vivo [Bruder et al. (1988) Clin. Orthop., 355 Suppl, S247-S256].

Also to be considered in fibrous regeneration and/or de novo formation is the importance of biocompatible polymers. A mimic of fibrous tissue is a hydrogel, a hydrophilic polymer capable of absorbing biological fluids while maintaining a three-dimensional structure [Lee et al. (2001) Chem. Rev. 101:1,869-1,879]. Hydrogel scaffolds can provide tissue-forming cells, such as chondrocytes, with a mimicked environment of the extracellular matrix. [Oxley et al. (1993) Biomaterials 14:1064-1072]. A large number of hydrogel polymers have been widely utilized in fibrous tissue engineering including alginate, polylactic acid (PLA), polyglycolic acid (PGA) or their copolymer (PLGA), chitosan, and poly-ethylene glycol-based polymers (PEG) [Lee (2001) Chem. Rev., 101:1,869-1,879]. Gelatin and collagen are preferred biocompatible scaffolds for use herein.

In one preferred aspect, the biocompatible scaffold is layered from two or more biocompatible scaffolds. One preferred layered biocompatible scaffold is comprised of gelatin sandwiched between two collagen sponges; i.e., first and third layers comprised of collagen sponge and a second, middle, layer comprised of gelatin. In another preferred embodiment, gelatin constitutes the two outer layers and collagen comprises the middle layer.

Preferably, one or both of the outer layers, when present such as the illustrative collagen sponge layers include a collagenic effective amount of absorbed growth factor protein(s) as can be prepared by soaking one or both sponge layers in a solution of BMP. Illustrative growth factors include recombinant human bone morphogenic protein 2 (rhBMP-2) or another of the BMPs of which about twenty are known and are discussed below. The growth factor can also be provided by MSCs that are dispersed in the scaffold.

It is thus seen that MSCs, or other stem cells, can serve one or both of two functions in the present invention. In one function, those cells are precursors to the fibroblast cells and can be used in place of fibroblasts. In another function, MSCs are the source of the growth factor cytokine that interacts with the fibroblasts to stimulate their growth into the soft connective tissue.

A wide variety of growth factor proteins can be used in the present invention. Growth factors are proteins that can activate cellular proliferation and/or differentiation. Preferred growth factors are collagenic, and include members of the transforming growth factor β (TGFβ) family, which family has proliferative effects on many mesenchymal and epithelial cell types. This family of growth factors includes the bone morphogenic proteins, some of which are also referred to as osteogenic proteins (OP) and are similarly given numerical suffixes, and the so-called growth/differentiation factors (GDFs) that also are given numerical suffixes.

Members of the transforming growth factor β family that are preferred include bone morphogenetic protein 2 (BMP-2); bone morphogenetic protein 4 (BMP-4); and transforming growth factors β-1, β-2, and β-3 (potent keratinocyte growth factors). Other useful members of the transforming growth factor β family include BMP-3, BMP-5, BMP-6, BMP-9, DPP, Vgl, Vgr, 60A protein, GDF-1, GDF-3, GDF-5, GDF-6, GDF-7, CDMP-1, CDMP-2, CDMP-3 (BMP-12; GDF-7), BMP-10, BMP-11, BMP-13 (GDF-6; CDMP-2), BMP-15, Univin, Nodal, Screw, ADMP, Neural, and amino acid sequence variants thereof. Other preferred growth factors include epidermal growth factor (EGF), which induces proliferation of both mesodermal and ectodermal cells, particularly keratinocytes and fibroblasts; platelet-derived growth factor (PDGF), which exerts proliferative effects on mesenchymal cells; fibroblast growth factor (FGF), both acidic and basic; and insulin-like growth factor 1 (IGF-1) and 2 (IGF-2), which mediate the response to growth hormone, particularly in bone growth.

Further preferred growth factors include osteogenic proteins. A particularly preferred osteogenic protein is OP-1, also known as bone morphogenetic protein 7 (BMP-7). OP-1 is a member of the transforming growth factor β gene superfamily. It is a 139 amino acid residue long homodimer of MW 36,000. OP-1 induces new bone formation in vivo and promotes the repair of diaphyseal segmental bone defects. Another particularly preferred growth factor is BMP-2. This protein is a 114 amino acid residue long in its mature form and is obtained as a glycosylated homodimer of MW 18,000.

An effective amount of growth factor protein(s) is utilized in a contemplated composition. For the preferred BMP-2 protein, that amount is about 0.5 to about 15 µg per 15 µl. That amount can vary for other collagenic proteins, but a useful collagenic amount can be readily determined using BMP-2 as a reference.

An effective amount of growth factor(s) can be determined by, for example, assaying for the amount of sulfated proteoglycans in a growth factor treated sample using the DMMB dye assay. [Hauselmann et al. (1994) *J. Cell. Sci.*, 107:17-27.] Alternative assays for collagenic amounts of growth factors are well known in the art.

Most preferably, the connective tissue is prepared in vivo by an implant into a host animal. The implant is comprised of autologous fibroblastic cells contained within a biocompatible scaffold comprised of gelatin that is sandwiched between two microporous collagen sponges loaded with recombinant human bone morphogenic protein 2 (rhBMP-2).

Illustrative host animals in which the fibrous tissue can be grown include laboratory animals such as rat, mouse and rabbit, a companion animal such as a dog or cat, a veterinary animal such as a horse (equine), cow (bovine), sheep (ovine) or goat (caprine), or an primate such as a monkey, ape (chimp, orangutan or gorilla) or man.

Another embodiment of the present invention is directed to a composition comprising collagenous precursor cells that are fibroblastic cells admixed with (seeded in) a biocompatible scaffold. Preferably, in this composition, the fibroblastic cells are autologous. Also, it is preferred that the biocompatible scaffold part of the composition comprises gelatin that is sandwiched between two collagen sponges. More preferably, one or both of the sponge layers contain recombinant human bone morphogenic protein 2 (rhBMP-2).

In a preferred embodiment, the scaffold of the composition comprises a material selected from the group consisting of polylactic acid, polyglycolic acid, polyethylene glycol diacrylate, polyethylene glycol dimethacrylate and mixtures thereof. More preferably, the scaffold of the composition is a natural material selected from the group consisting of alginate, chitosan, coral, agarose, fibrin, collagen, gelatin, bone, silicone, cartilage, hydroxyapatite, calcium phosphate, and mixtures thereof.

A further aspect of the present invention contemplates a method of producing connective tissue comprising the steps of harvesting fibroblastic cells; loading the cells onto a biocompatible scaffold to form a composition; and implanting the composition into a host.

In a more preferred method, the biocompatible scaffold comprises gelatin layered between two (rhBMP-2 protein)-soaked collagen sponge layers or a collagen sponge layered between two layers of (rhBMP-2 protein)-soaked gelatin.

In another preferred embodiment, a method of producing cranial sutures in vivo is described that comprises implanting into a host a composition comprising a biocompatible scaffold and autologous fibroblastic cells. Preferably, in this embodiment, the scaffold is comprised of gelatin sandwiched between two collagen sponges that have been soaked in recombinant human bone morphogenic protein 2.

Example 1

Synthesis of Cranial Sutures in Vivo

A. Isolation of Dermal Fibroblasts and Fabrication of Fibroblastic Composition

Eight, 8-week-old, male, New Zealand White rabbits were used in the isolation of dermal fibroblasts after approval by the Animal Care Committee of the University of Illinois at Chicago. Under general anesthesia and aseptic conditions, a 5-mm incision was made in the anterior tibial skin of the rabbit (FIG. 1A). A small piece of subcutaneous fibrous tissue (approx. 3×3 mm$^2$) was removed, minced and digested with the enzyme Accutase under 37° C. for 1 hour, followed by neutralization with Dulbecco's Modified Eagle's Medium-Low Glucose (DMEM; Sigma, St. Louis, Mo.) supplemented with 10% fetal bovine serum (FBS) (Biocell, Rancho Dominguez, Calif.) (FIG. 1B).

Figure 2:
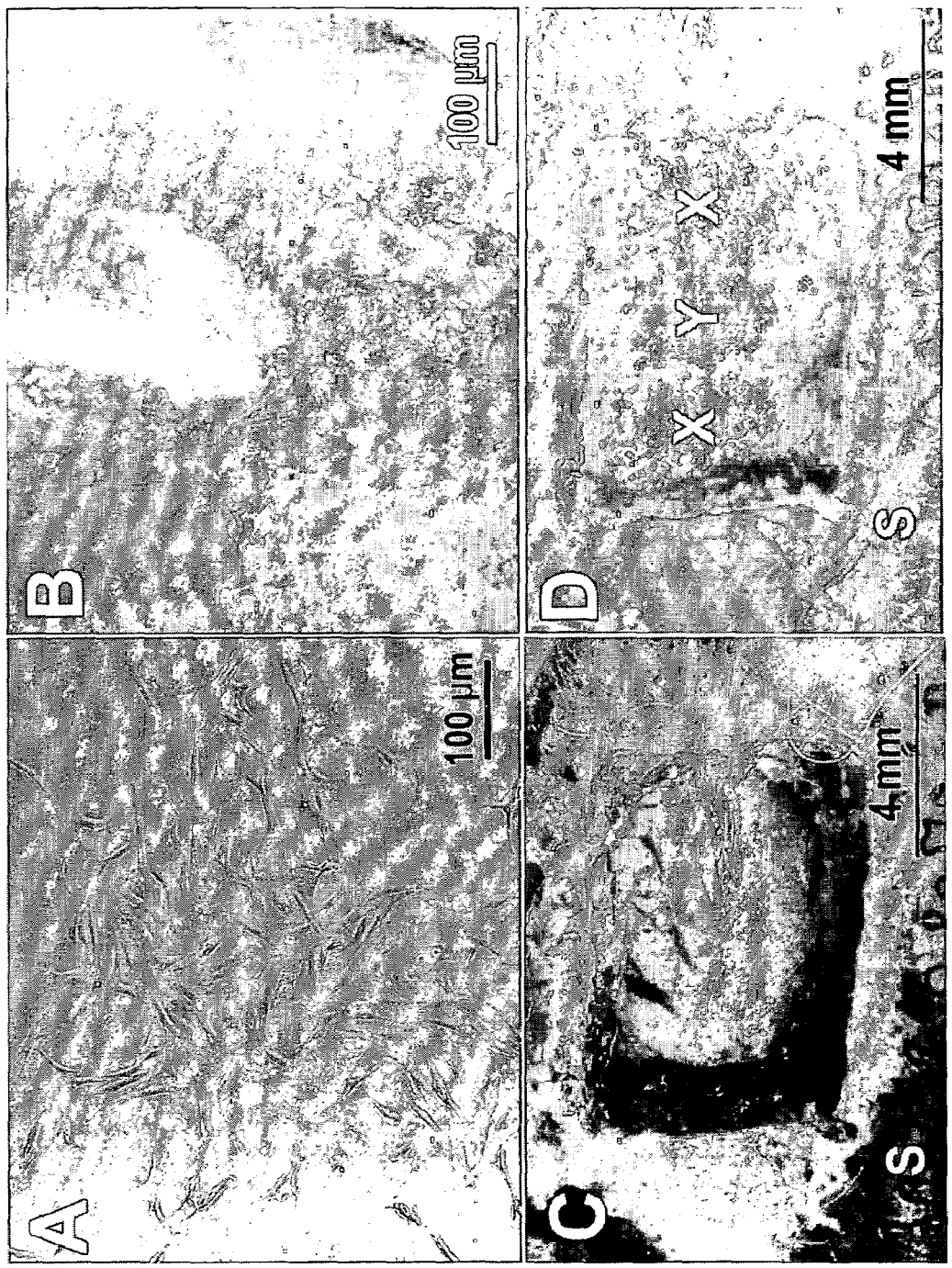
FIG. 2, in parts 2A-2D, shows the results of the culture, expansion, and seeding of autologous dermal fibroblasts in gelatin scaffold and surgical creation of calvarial defects. 2A: Dermal fibroblasts isolated subcutaneously from the anterior tibia were culture-expanded and possessed typical spindle shape. 2B: Seeding of culture-expanded dermal fibroblasts in gelatin scaffold that was porous to allow cell migration into the scaffold. 2C: Surgical creation of full-thickness calvarial defect with a dimension of 6×2×8 mm$^3$ in the center of the rabbit parietal bone devoid of natural cranial sutures. The adjacent sagittal suture (s) is shown. The dura mater was kept intact. 2D: The surgically created calvarial defect was filled with a composition consisting of autologous dermal fibroblast-seeded gelatin scaffold (Y component) that was sandwiched between two rhBMP-2 soaked microporous collagen sponges (X components). The adjacent sagittal suture (s) was not a part of surgically created calvarial defect.

The digested tissue solution was filtered through a cell restrainer (100 µm pore size). After centrifugation, the isolated dermal fibroblasts were plate-cultured (106 cells/100 mm dish) and expanded in DMEM with 10% FBS and 1% antibiotic-antimycotic (Gibco, Carlsbad, Calif.) (FIGS. 1C and 2A). Upon 90% confluency, the fibroblasts were trypsinized and subcultured at a density of 106 cells/100 mm dish (FIG. 2A). An absorbable gelatin scaffold (Pharmacia, Kalamazoo, Mich.) was trimmed into 2×2×6 mm$^3$ and immersed in cell suspension at 107 cells/ml in DMEM supplemented with 10% FBS under a light vacuum created by a 20 ml syringe for 1 hr (FIG. 1D, 1E and 2B), followed by 2-hour incubation at 37° C.

B. Preparation of Biocompatible Scaffold and Fabrication of Fibroblast Composition Absorbable collagen hemostatic sponges (Integra, Plainsboro, N.J.) were each trimmed into 3×2×6 mm$^3$ size (FIG. 1F and 1G). Recombinant human bone morphogenetic protein-2 (rhBMP-2; R&D Systems, Minneapolis, Minn.) was prepared by dissolving 2.5 µg rhBMP-2 in 15 µl PBS at 4° C. overnight (about 18 hours; FIG. 1F). The rationale for incorporating BMP-2 was to simulate the high osteogenic potential of synostosed cranial sutures (De Pollack et al., 1996). The fibroblasts, as prepared above were sandwiched between two rhBMP-2 soaked collagen sponges to create a fibroblast composition with a dimension of 6×2×8 mm$^3$ (FIG. 1G).

C. Implantation of Fibroblast Composition

Under aseptic conditions and general anesthesia with ketamine (40 mg/kg) and xylazine (8 mg/kg), a 2-cm incision was made along the midsagittal plane in the calvarium of a host rabbit. Upon deflection of the scalp, subcutaneous tissue and periosteum, a full-thickness calvarial defect (6×2×8 mm$^3$) was created unilaterally in the center of the parietal bone using a dental bur with constant PBS irrigation (FIG. 2C). Care was taken to ensure that the surgically created full-thickness calvarial defect was devoid of the adjacent coronal, sagittal or lamboidal suture, and also to maintain the underlying dura mater intact (FIG. 2C). The fibroblast composition discussed before (FIG. 1G) was implanted into the surgically created calvarial defect of the corresponding donor rabbit from which the dermal fibroblasts had been harvested and culture-expanded (N=4) (FIG. 2D). The same procedures were performed in each of four additional age- and sex-matched rabbits with the only exception that no dermal fibroblasts or gelatin scaffold were incorporated between two rhBMP2-soaked collagen sponges in the surgically created calvarial defect (no Y component in FIG. 2D) (N=4). Then, the previously deflected periosteum, subcutaneous tissue and scalp were replaced. The incision was closed with 4-0 absorbable gut surgical suture. The rabbits were housed in a temperature and light controlled room (23-25° C., 14 hr light/day), and given standard daily amounts of food and water.

D. Assessment of in Vivo Formation of Soft Connective Tissue (i.e. cranial Sutures)

Four weeks after in vivo implantation, all rabbits were euthanized by pentobarbital overdose (300 mg/kg, i.v.). The entire calvarium was harvested with an orthopedic saw, fixed in 10% paraformaldehyde, demineralized in equal volumes of 20% sodium citrate and 50% formic acid, and embedded in paraffin. Serial 8-μm thick sections were cut in the parasagittal plane using a microtome. Mineral deposition in surgically implanted grafts was grossly examined by radiophotographic imaging at 90 kV and 15 mA with 10 s exposure. Three 8-μm thick microscopic sections in the parasagittal plane were stained with hematoxylin and eosin: one from the center of the implanted graft and two from both sides of graft each 2 mm from the parasagittal midline. Quantitative histomorphometric analysis was performed on H & E stained microscopic sections under a research microscope with a digital camera. The widths of the fibrous interface between two active bone formation fronts were measured from no less than 6-8 lines per specimen using computerized image analysis (cf., FIG. 3D). The average widths of the fibrous interface (f in FIG. 3D) in the tissue were compared between those with seeded dermal fibroblasts in gelatin scaffold and those without dermal fibroblasts or gelatin scaffold by using Student's T tests at an alpha level of $P<0.05$.

Figure 3:
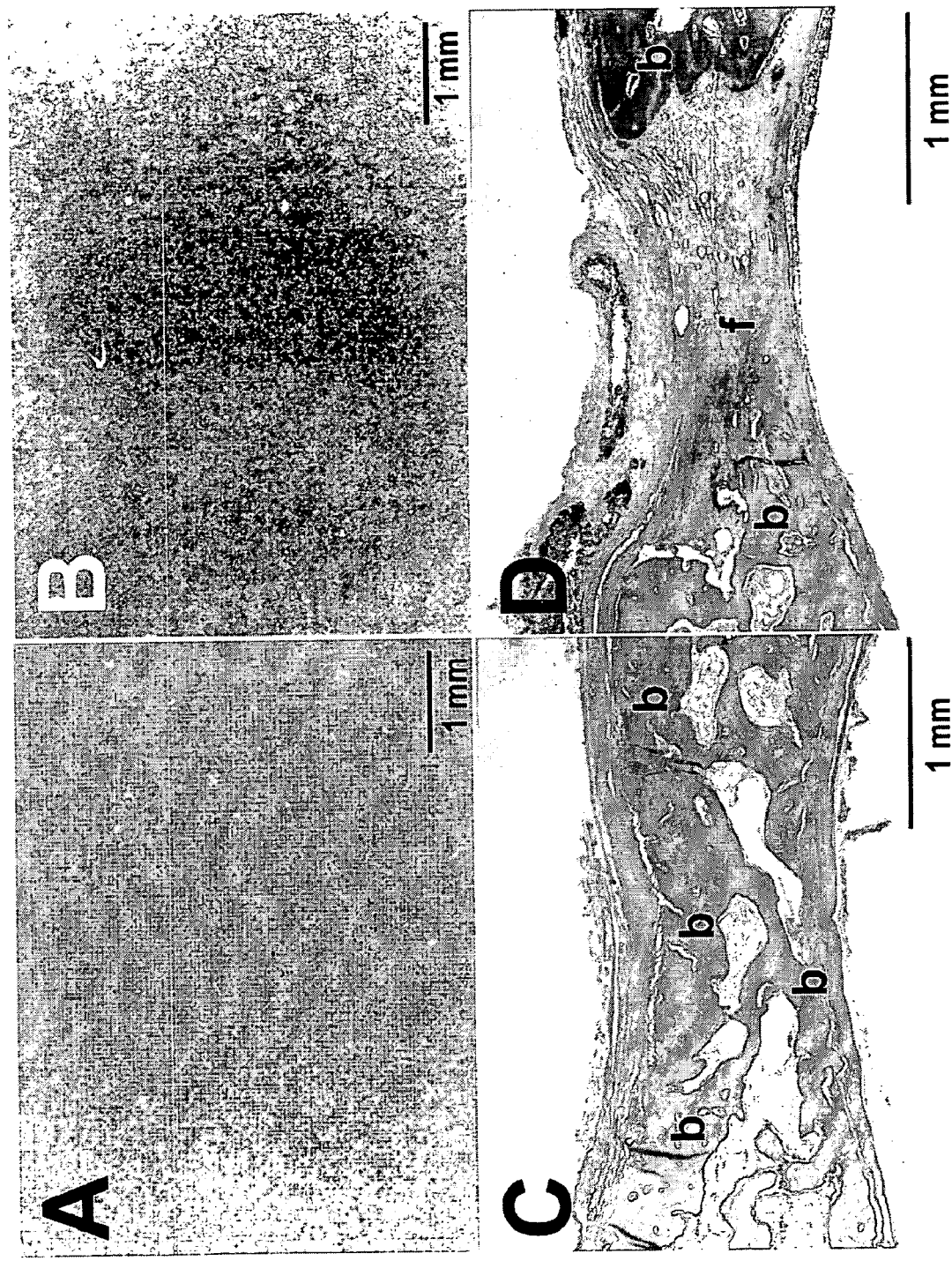
FIG. 3, in parts 3A-3D, illustrates radiographic and photomicrographic images of surgically created calvarial defects filled with two rhBMP-soaked collagen sponges (A and C) and with a composition consisting of fibroblast-seeded gelatin scaffold sandwiched between two rhBMP-soaked collagen sponges (B and D). 3A: Representative radiographic image of a surgically created calvarial defect filled with two rhBMP-soaked collagen sponges. A lack of radiolucency indicates thorough mineralization in the surgically created calvarial defect. 3B: Representative radiographic image of a surgically created calvarial defect filled with fibroblast-seeded gelatin scaffold sandwiched between two rhBMP-soaked collagen sponges. A band of radiolucency in (B) suggests a non-mineralized gap between mineralized bone. 3C: Representative photomicrographic image of a microscopic section corresponding to A showing complete bony fusion (b) occurred in the calvarial defect filled with tissue grafts consisting of two rhBMP-soaked collagen sponges but without intervening fibroblast-seeded gelatin scaffold. 3D: Representative photomicrographic image of a microscopic section corresponding to B showing de novo formation of a fibrous tissue interface (f) between two mineralized bone segments (b) in the calvarial defect filled with fibroblast-seeded gelatin scaffold sandwiched between two rhBMP-soaked collagen sponges.

The results from radiographic examination revealed a lack of radiolucency in the tissue with two rhBMP-2 soaked microporous collagen sponges lacking a fibroblast-seeded gelatin scaffold (FIG. 3A). By contrast, a band of radiolucency was present in the center of each of the tissues synthesized from the fibroblast composition consisting of a fibroblast-seeded gelatin scaffold sandwiched between two rhBMP-2 soaked microporous collagen sponges (FIG. 3B). Microscopic sections corroborated radiographic images by demonstrating complete osseous fusion of the tissue consisting of two rhBMP-2 soaked microporous collagen sponges without seeded dermal fibroblasts (FIG. 3C).

Figure 4:
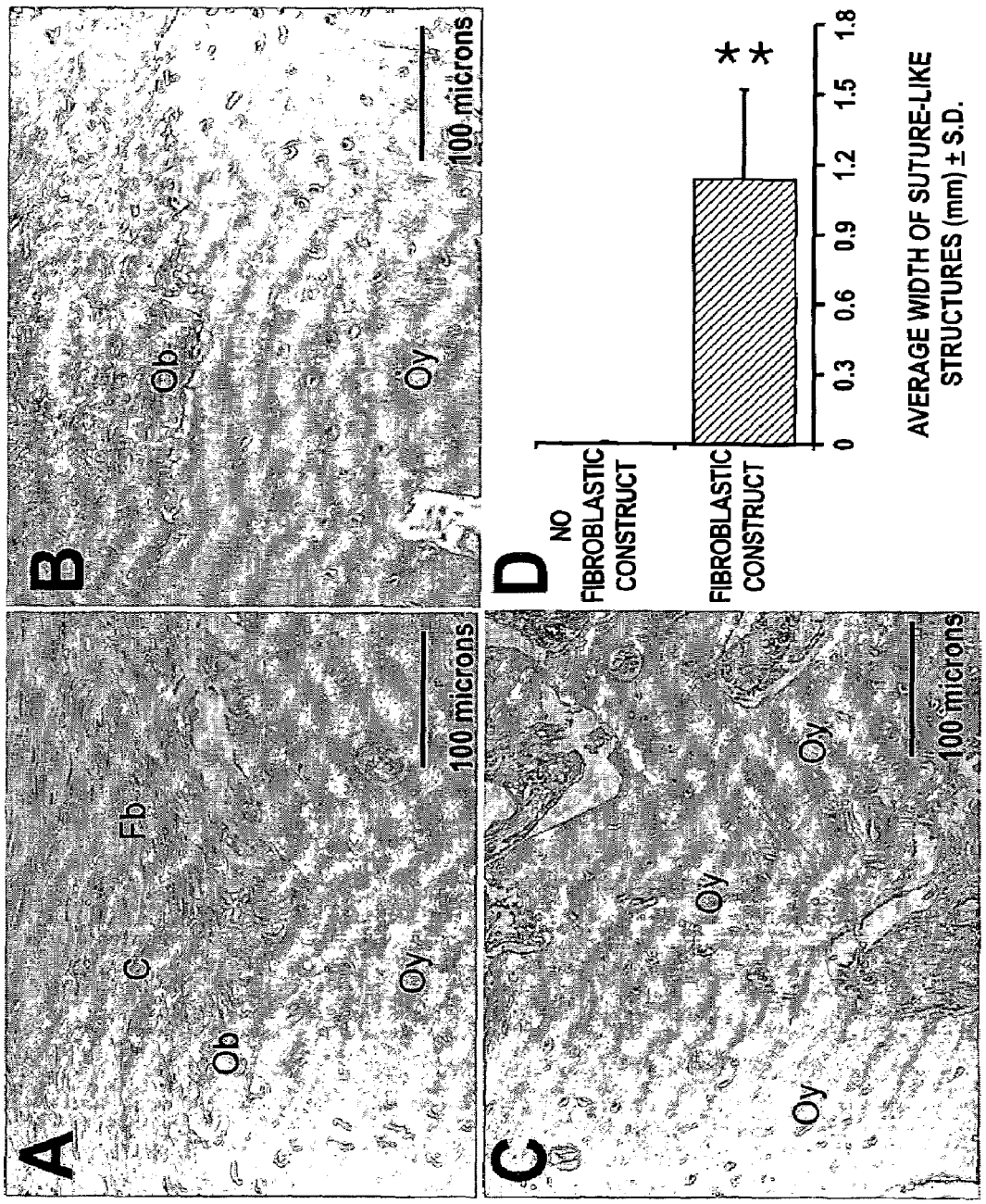
FIG. 4, in parts 4A-4D, shows high power examination of the suture-like structure. 4A: The suture-like structure consisted of collagen fiber-like structures (c), fibroblast-like cells (Fb), osteoblast-like cells (Ob) and osteocyte-like cells (Oy) in apparently mineralized bone. Osteoblast-like cells formed an approximate layer on the surface of apparent bone formation front. 4B: The adjacent natural sagittal suture showed fibroblast-like cells in suture mesenchyme, osteoblasts lining up the sutural bone formation front and osteocytes (Oy) in the mineralized bone. 4C: Complete bony fusion occurred in the surgically created calvarial defect filled with tissue grafts consisting of two rhBMP-soaked collagen sponges but without the intervening fibroblast-seeded gelatin scaffold. 4D: Histomorphometric analysis and statistical comparison of the widths of the fibrous tissue interface between two mineralized bone formation fronts. The average width of suture-like structures consisting of dermal fibroblast-populated gelatin scaffold sandwiched between two rhBMP-2 soaked microporous collagen sponges was 1.13±0.39 mm (S.D.), significantly greater than the average width of the tissue-engineered grafts without intervening dermal fibroblast scaffolds (0.006±0.004 mm). **:P<0.01.

In comparison, the fibroblast composition consisting of a dermal fibroblast-seed gelatin scaffold sandwiched between two rhBMP-2 soaked microporous collagen sponges consistently demonstrated a fibrous tissue interface (f in FIG. 3D) between the two osteogenic bone formation fronts (b in FIG. 3D). High-power microscopic examination of the cranial suture indicated de novo formation of a fibrous tissue interface between two apparently new bone formation fronts in the surgically created calvarial defects devoid of natural cranial sutures (FIG. 4A). Fibroblast-like cells resided among apparently collagen fibers with areas of angiogenesis in the cranial suture (FIG. 4A). Columnar osteoblast-like cells lined up the surface of the bone formation front with osteocyte-like cells embedded in mineralized bone that possessed distinct lacunae-like structures (FIG. 4A). These microscopic characteristics of the cranial suture structure were similar to the adjacent natural sagittal suture in which osteogenic cells lined up the surface of sutural bone formation front with embedded osteocytes also possessing lacunae (FIG. 4B).

In comparison with the cranial suture structure in FIG. 4A, tissue grafts consisting of two rhBMP-2 soaked collagen sponges lacking the intervening fibroblastic gelatin scaffold led to virtually complete ossification of the surgically created defect (FIG. 4C). Histomorphometric data measured from multiple microscopic sections demonstrated that the average width of cranial suture structures consisting of dermal fibroblast-populated gelatin scaffold sandwiched between two rhBMP-2-soaked microporous collagen sponges was 1.13±0.39 mm (S.D.), significantly greater than the average width of tissue grafts without intervening dermal fibroblast-gelatin scaffolds (0.006±0.004 mm)(FIG. 4D).

The present findings represent the first report of de novo formation of cranial suture structure from autologous cells based on the following: First, a cranial suture structure is only created in the surgically created calvarial defect in the presence of a fibroblast composition including fibroblast-seeded gelatin scaffold intervening between two rhBMP2 soaked collagen sponges. Second, osteoblast-like cells line up the bone formation fronts, indicating that the cranial suture structure is not fibrous non-union. Third, the microscopic characteristics of the cranial suture structure are similar to the adjacent natural suture. Fourth, up to 4 weeks of in vivo implantation, the cranial suture structure remains patent without complete ossification.

By contrast, calvarial defects filled with tissue grafts consisting of two rhBMP2-soaked collagen sponges but without intervening fibroblast-gelatin scaffold readily ossify. The makeup of cells in natural suture mesenchyme is not entirely clear, although there are multiple cell types such as neural crest-derived mesenchymal cells, fibroblast-like cells, osteoblast-like cells, and any blood-vessel borne cells (Rice et al., 1999; Wilkie and Morriss-Kay, 2001). Type I collagen is the most abundant collagen phenotype in cranial sutures (Meikle et al., 1982; Yen et al., 1989; Takahashi et al., 1996; Rafferty and Herring, 1999; Zimmerman et al., 1998; Cohen, 2000). Thus, sutures likely contain cells that produce type I collagen fibrils.

The fact that suture mesenchyme is not ossified during suture patency indicates the presence of cells in suture mesenchyme capable of producing non-mineralizing type I collagen. Accordingly, autologous fibroblasts were delivered in the present fibroblast composition. The presently delivered fibroblasts are autologous in that sutures are formed de novo in rabbits from which dermal fibroblasts have been isolated. This autologous approach may eliminate the potential problem of immune rejection by allografts or xenografts. The osteogenic cells lining up the osteogenic fronts in the cranial suture structures can derive from the overlying periosteum or underlying dura mater, or mesenchymal cells resident in the dermal fibroblast population that differentiated into osteogenic cells in the presence of rhBMP-2.

The exogenously delivered rhBMP-2, known as a potent osteo-inductive factor, may have multiple effects. The rationale for incorporating BMP-2 is to simulate the high osteogenic potential of synostosed cranial sutures (De Pollack et al., 1996). The bone formation rate of synostosed sutures can be 50% higher than that of normal sutures (De Pollack et al., 1996). Even in the presence of rhBMP-2, dermal fibroblasts seeded in gelatin scaffold intervening between two BMP-2 soaked collagen sponges are capable of maintaining the presence of the cranial suture structure. Application of rhBMP-2 may also have implications in providing osteogenic stimulation in the adult craniosynostosis patient due to potential shortage of bone as a result of reshaping of skull bones.

Furthermore, application of certain doses of TGFβ-3 soaked in collagen gel placed between the suture and overlying periosteum delays the timed fusion of the rat interfrontal suture (Opperman et al, 1999 and 2002), further substantiating the potential role TGFβ superfamily plays in regulating sutural fusion (Bradley et al., 2000; Greenwald et al, 2000; Moursi et al., 2003). This important approach of growth factor delivery by encapsulating growth factors in tissue-engineered composite constructs has been previously developed in other circumstances (Hong et al., 2000).

From the foregoing, it will be observed that numerous modifications and variations can be effected without departing from the true spirit and scope of the present invention. It is to be understood that no limitation with respect to the specific examples presented is intended nor should be inferred. The disclosure is intended to cover by the appended claims modifications as fall within the scope of the claims.

Each of the patents and articles cited herein is incorporated by reference. The use of the article "a" or "an" is intended to include one or more.

What is claimed:

1. A method of producing connective tissue in a subject comprising:
   (a) providing a biocompatible scaffold and precursor cells, wherein
      the biocompatible scaffold comprises a gelatin layer that is sandwiched between two collagen sponge layers or a collagen layer sandwiched between two gelatin layers, and
      the precursor cells are seeded in the biocompatible scaffold; and
   (b) implanting the scaffold into the subject.

2. The method of claim 1 wherein the connective tissue is a cranial suture or periodontal ligament.

3. The method of claim 1 wherein the scaffold further comprises a growth factor.

4. The method of claim 3 wherein said growth factor is a member of the TGF-β family of proteins.

5. The method of claim 1 wherein said precursor cells are autologous fibroblastic cells or fibroblast-like cells.

6. The method of claim 1 wherein said precursor cells are stem cells.

7. The method of claim 6 wherein said stem cells are adult stem cells.

8. The method of claim 7 wherein said adult stem cells are adult mesenchymal stem cells.

9. The method of claim 1 wherein the biocompatible scaffold comprises a gelatin layer sandwiched between two collagen sponge layers, wherein one or both collagen sponge layers contains a growth factor protein that is a member of the TGF-β family of proteins, wherein the growth factor protein is present in an amount effective to activate proliferation and/or differentiation of the precursor cells.

10. The method of claim 9 wherein both collagen sponge layers contain rhBMP-2 as the member of the TGF-β family of proteins.

11. The method of claim 9 wherein said precursor cells are autologous fibroblastic cells or fibroblast-like cells.

12. The method of claim 9 wherein the biocompatible scaffold further comprises a material selected from the group consisting of polylactic acid, polyglycolic acid, polyethylene glycol and mixtures thereof.

13. The method of claim 9 wherein the biocompatible scaffold further comprises a material selected from the group consisting of alginate, chitosan, coral, agarose, fibrin, collagen, gelatin, bone, silicone, cartilage, hydroxyapatite, calcium phosphate, and mixtures thereof.

14. The method of claim 1 wherein the precursor cells are fibroblastic cells and one or both collagen sponge layers contains a member of the TGF-β family of proteins in an amount effective to promote production of extracellular matrix by the cells.

15. The method of claim 3 wherein the growth factor is a bone morphogenetic protein, a transforming growth factor, DPP, Vgl, Vgr, 60A protein, growth differentiation factor (GDF)-1, GDF-3, GDF-5, GDF-6, GDF-7, cartilage-derived morphogenic protein (CDMP)-1, CDMP-2, CDMP-3, Univin, Nodal, Screw, anti-dorsalizing morphogenetic protein (ADMP), Neural, epidermal growth factor (EGF), platelet-derived growth factor (PDGF), acidic fibroblast growth factor (FGF), basic FGF, insulin-like growth factor (IGF)-1, or IGF-2.

16. The method of claim 3 wherein the growth factor is a bone morphogenic protein.

17. The method of claim 16 wherein the bone morphogenic protein is human bone morphogenic protein 2.

18. The method of claim 1 wherein the subject is a rat, mouse, rabbit, dog, cat, equine, bovine, ovine, goat, monkey, ape, or human.

19. The method of claim 1 wherein the subject is a human.

* * * * *

UNITED STATES PATENT AND TRADEMARK OFFICE
CERTIFICATE OF CORRECTION

PATENT NO.         : 7,709,442 B2                                                              Page 1 of 1
APPLICATION NO.    : 12/119631
DATED              : May 4, 2010
INVENTOR(S)        : Jeremy Jian Mao It is certified that error appears in the above-identified patent and that said Letters Patent is hereby corrected as shown below:

Col. 1 Line 15-18
Corrected Government Support paragraph:

This invention was made with government support under DE13964 and DE15391 awarded by the National Institute of Dental and Craniofacial Research of the National Institutes of Health. The government has certain rights in the invention.

Signed and Sealed this

Ninth Day of November, 2010

David J. Kappos
*Director of the United States Patent and Trademark Office*